(12) United States Patent
Tomberg et al.

(10) Patent No.: US 10,949,456 B2
(45) Date of Patent: Mar. 16, 2021

(54) METHOD AND SYSTEM FOR MAPPING TEXT PHRASES TO A TAXONOMY

(71) Applicant: KNOWTIONS RESEARCH INC., Toronto (CA)

(72) Inventors: Alexandre Tomberg, Toronto (CA); Rohollah Soltani Bidgoli, Toronto (CA)

(73) Assignee: KNOWTIONS RESEARCH INC., Toronto (CA)

( * ) Notice: Subject to any disclaimer, the term of this patent is extended or adjusted under 35 U.S.C. 154(b) by 0 days.

(21) Appl. No.: 16/833,559

(22) Filed: Mar. 28, 2020

(65) Prior Publication Data
US 2020/0311115 A1 Oct. 1, 2020

Related U.S. Application Data

(60) Provisional application No. 62/825,975, filed on Mar. 29, 2019.

(51) Int. Cl.
*G06F 16/35* (2019.01)
*G06N 5/04* (2006.01)
*G06N 20/00* (2019.01)
*G16H 10/60* (2018.01)

(52) U.S. Cl.
CPC ........... *G06F 16/355* (2019.01); *G06N 5/04* (2013.01); *G06N 20/00* (2019.01); *G16H 10/60* (2018.01)

(58) Field of Classification Search
CPC ...... G06F 16/355; G16H 10/60; G06N 20/00; G06N 5/04
See application file for complete search history.

(56) References Cited

U.S. PATENT DOCUMENTS

| | | | |
|---|---|---|---|
| 10,509,863 B1 | 12/2019 | Arfa et al. | |
| 2015/0339299 A1* | 11/2015 | Bagchi | G06F 16/3346 707/728 |
| 2016/0147891 A1* | 5/2016 | Chhichhia | G06F 16/986 707/734 |
| 2016/0358094 A1* | 12/2016 | Fan | G06F 16/3344 |
| 2017/0092265 A1* | 3/2017 | Sainath | G06N 3/0445 |
| 2017/0199963 A1* | 7/2017 | Kondadadi | G06Q 10/10 |
| 2018/0046764 A1* | 2/2018 | Katwala | G06F 40/295 |

(Continued)

OTHER PUBLICATIONS

International Search Report for PCT/CA2020/050411, Canadian Intellectual Property Office, dated Jul. 15, 2020.

(Continued)

*Primary Examiner* — Matthew J Ellis
(74) *Attorney, Agent, or Firm* — Bhole IP Law; Anil Bhole; Marc Lampert

(57) ABSTRACT

There is provided systems and methods for mapping of text phrases to a taxonomy. In an aspect, the method including: receiving the corpus and the taxonomy; mapping the text phrases in the corpus to a set of word embeddings in a word embedding space, where each sequence of word embeddings corresponds to individual words in one of the text phrases; vectorizing the taxonomy to a set of node embeddings in a node embedding vector space; mapping the set of word embeddings to the set of node embeddings using a mapping function, the mapping function outputting points in the node embedding space associated with sequences in the word embeddings; and outputting the mapping function.

12 Claims, 9 Drawing Sheets

(56) References Cited

U.S. PATENT DOCUMENTS

| | | |
|---|---|---|
| 2018/0232443 A1 | 8/2018 | Delgo et al. |
| 2018/0285459 A1 | 10/2018 | Soni et al. |
| 2019/0251480 A1* | 8/2019 | Garcia Duran ........ G06N 20/00 |
| 2019/0258721 A1* | 8/2019 | Guo ........................ G06N 20/00 |
| 2019/0370273 A1* | 12/2019 | Frison ................. G06F 16/3347 |

OTHER PUBLICATIONS

Written Opinion for PCT/CA2020/050411, Canadian Intellectual Property Office, dated Jul. 15, 2020.

* cited by examiner

| Text2Node model | | | Accuracy (top $k$) | | | | |
|---|---|---|---|---|---|---|---|
| Mapping | Word Emb | Metric | $k=1$ | $k=5$ | $k=10$ | $k=20$ | $k=50$ |
| Linear | GloVe | cos | 0.033 | 0.106 | 0.163 | 0.231 | 0.352 |
| Linear | GloVe | $\ell_2$ | 0.014 | 0.062 | 0.099 | 0.153 | 0.245 |
| Linear | FastText | cos | 0.029 | 0.094 | 0.153 | 0.226 | 0.355 |
| Linear | FastText | $\ell_2$ | 0.012 | 0.050 | 0.091 | 0.143 | 0.237 |
| CNN | GloVe | cos | 0.061 | 0.176 | 0.249 | 0.338 | 0.485 |
| CNN | GloVe | $\ell_2$ | 0.045 | 0.150 | 0.214 | 0.294 | 0.419 |
| CNN | FastText | cos | 0.082 | 0.218 | 0.304 | 0.397 | 0.546 |
| CNN | FastText | $\ell_2$ | 0.067 | 0.181 | 0.256 | 0.350 | 0.495 |
| Bi-LSTM | GloVe | cos | 0.225 | 0.442 | 0.543 | 0.640 | 0.762 |
| Bi-LSTM | GloVe | $\ell_2$ | 0.195 | 0.402 | 0.497 | 0.602 | 0.722 |
| Bi-LSTM | FastText | cos | 0.239 | 0.466 | 0.571 | 0.671 | 0.785 |
| Bi-LSTM | FastText | $\ell_2$ | 0.201 | 0.416 | 0.515 | 0.616 | 0.744 |

*FIG. 6*

| Text2Node model | | | Mean graph distance (top $k$) | | | | |
|---|---|---|---|---|---|---|---|
| Mapping | Word Emb | Metric | $k=1$ | $k=5$ | $k=10$ | $k=20$ | $k=50$ |
| Linear | GloVe | cos | 2.08 | 2.23 | 2.30 | 2.35 | 2.42 |
| Linear | GloVe | $\ell_2$ | 1.79 | 2.07 | 2.17 | 2.24 | 2.32 |
| Linear | FastText | cos | 2.01 | 2.17 | 2.23 | 2.28 | 2.35 |
| Linear | FastText | $\ell_2$ | 1.78 | 2.06 | 2.16 | 2.23 | 2.31 |
| CNN | GloVe | cos | 1.71 | 1.95 | 2.03 | 2.11 | 2.19 |
| CNN | GloVe | $\ell_2$ | 1.60 | 1.88 | 1.98 | 2.06 | 2.14 |
| CNN | FastText | cos | 1.60 | 1.86 | 1.95 | 2.03 | 2.13 |
| CNN | FastText | $\ell_2$ | 1.52 | 1.80 | 1.91 | 2.00 | 2.09 |
| Bi-LSTM | GloVe | cos | 1.28 | 1.63 | 1.76 | 1.88 | 2.01 |
| Bi-LSTM | GloVe | $\ell_2$ | 1.26 | 1.61 | 1.74 | 1.86 | 1.98 |
| Bi-LSTM | FastText | cos | 1.27 | 1.61 | 1.75 | 1.87 | 2.01 |
| Bi-LSTM | FastText | $\ell_2$ | 1.25 | 1.59 | 1.73 | 1.85 | 1.98 |

*FIG. 7*

| Text2Node model | | Accuracy (top $k$) | | | | |
|---|---|---|---|---|---|---|
| Word Emb | Metric | $k=1$ | $k=5$ | $k=10$ | $k=20$ | $k=50$ |
| GloVe | cos | 0.202 | 0.430 | 0.541 | 0.644 | 0.755 |
| GloVe | $\ell_2$ | 0.170 | 0.394 | 0.501 | 0.602 | 0.714 |
| FastText | cos | 0.210 | 0.443 | 0.553 | 0.658 | 0.763 |
| FastText | $\ell_2$ | 0.181 | 0.403 | 0.507 | 0.614 | 0.725 |

*FIG. 8*

| Text2Node model | | Mean graph distance (top $k$) | | | | |
|---|---|---|---|---|---|---|
| Word Emb | Metric | $k=1$ | $k=5$ | $k=10$ | $k=20$ | $k=50$ |
| GloVe | cos | 1.42 | 1.74 | 1.88 | 2.00 | 2.14 |
| GloVe | $\ell_2$ | 1.40 | 1.72 | 1.85 | 1.97 | 2.10 |
| FastText | cos | 1.40 | 1.73 | 1.87 | 1.99 | 2.14 |
| FastText | $\ell_2$ | 1.36 | 1.69 | 1.84 | 1.95 | 2.09 |

*FIG. 9*

| Text2Node model | | Accuracy (top $k$) | | | | |
|---|---|---|---|---|---|---|
| Word Emb | Metric | $k=1$ | $k=5$ | $k=10$ | $k=20$ | $k=50$ |
| GloVe | cos | 0.379 | 0.698 | 0.793 | 0.855 | 0.905 |
| GloVe | $\ell_2$ | 0.350 | 0.655 | 0.754 | 0.822 | 0.876 |
| FastText | cos | 0.389 | 0.710 | 0.804 | 0.863 | 0.914 |
| FastText | $\ell_2$ | 0.362 | 0.658 | 0.760 | 0.829 | 0.887 |

*FIG. 10*

| Text2Node model | | Mean graph distance (top $k$) | | | | |
|---|---|---|---|---|---|---|
| Word Emb | Metric | $k=1$ | $k=5$ | $k=10$ | $k=20$ | $k=50$ |
| GloVe | cos | 1.32 | 1.80 | 1.98 | 2.13 | 2.29 |
| GloVe | $\ell_2$ | 1.36 | 1.82 | 1.98 | 2.12 | 2.26 |
| FastText | cos | 1.27 | 1.78 | 1.98 | 2.13 | 2.28 |
| FastText | $\ell_2$ | 1.31 | 1.80 | 1.97 | 2.11 | 2.25 |

*FIG. 11*

| Text2Node model | | Accuracy (top $k$) | | | | |
|---|---|---|---|---|---|---|
| Word Emb | Metric | $k=1$ | $k=5$ | $k=10$ | $k=20$ | $k=50$ |
| GloVe | cos | 0.242 | 0.449 | 0.538 | 0.622 | 0.737 |
| GloVe | $\ell_2$ | 0.227 | 0.391 | 0.481 | 0.583 | 0.706 |
| FastText | cos | 0.221 | 0.499 | 0.591 | 0.671 | 0.780 |
| FastText | $\ell_2$ | 0.186 | 0.439 | 0.534 | 0.636 | 0.734 |

*FIG. 12*

| Text2Node model | | Mean graph distance (top $k$) | | | | |
|---|---|---|---|---|---|---|
| Word Emb | Metric | $k=1$ | $k=5$ | $k=10$ | $k=20$ | $k=50$ |
| GloVe | cos | 1.41 | 1.74 | 1.86 | 1.97 | 2.09 |
| GloVe | $\ell_2$ | 1.38 | 1.70 | 1.82 | 1.93 | 2.04 |
| FastText | cos | 1.41 | 1.69 | 1.81 | 1.92 | 2.05 |
| FastText | $\ell_2$ | 1.38 | 1.65 | 1.78 | 1.88 | 2.00 |

*FIG. 13*

METHOD AND SYSTEM FOR MAPPING TEXT PHRASES TO A TAXONOMY

FIELD OF THE INVENTION

The following relates generally to the mapping of general text phrases to a fixed taxonomy, and more specifically to computer-based method and system for mapping text phrases to a medical language taxonomy.

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

Electronic health and medical record (EHR/EMR) systems are steadily gaining in popularity. Ever more facets of healthcare are recorded and coded in such systems, including patient demographics, disease history and progression, laboratory test results, clinical procedures and medications, and even genetics. This trove of information is a unique opportunity to learn patterns that can help improve various aspects of healthcare. However, the sheer number of various coding systems used to encode this clinical information is a major challenge for anyone trying to analyze structured EHR data. Even the most widely used coding systems have multiple versions to cater to different regions of the world. Software developed to analyze one version of the coding system may not be used for another version, let alone a different coding system. In addition to the public and well documented coding systems, a multitude of private coding mechanisms that have no mappings to any public coding systems are used by insurance companies and certain hospitals.

The efforts to solve this problem range from the development of mapping dictionaries between coding systems to machine learning driven approaches. One example of the former is cTAKES, a project that uses annotated lookup tables to map clinical entities to concepts in a controlled vocabulary such as SNOMED CT (Systematised Nomenclature of Medicine—Clinical Terms). The reliance of cTAKES and similar systems on symbolic natural language processing techniques makes them hard to generalize and scale, especially in view of regular updates and changes to the target vocabulary. An example of the latter approach is work where word embeddings have been used in a hierarchical structure to annotate and map medical concepts to a reference taxonomy. Their method is based on classification learning and limited in its ability to be applied on controlled vocabularies such as SNOMED CT due to the large size of these vocabularies and small number of terms or phrases associated with each concept.

SUMMARY OF THE INVENTION

In an aspect, there is provided a computer-implemented method for mapping of text phrases in a corpus to a taxonomy, the method comprising: receiving the corpus and the taxonomy; mapping the text phrases in the corpus to a set of word embeddings in a word embedding space, where each sequence of word embeddings corresponds to individual words in one of the text phrases; vectorizing the taxonomy to a set of node embeddings in a node embedding vector space; mapping the set of word embeddings to the set of node embeddings using a mapping function, the mapping function outputting points in the node embedding space associated with sequences in the word embeddings; and outputting the mapping function.

In a particular case of the method, the method further comprising pre-processing the corpus, the pre-processing comprising at least one of splitting phrases into words, splitting sentences, adding spaces around punctuation marks, changing characters to lowercase, reformatting to one sentence per line, and concatenating files.

In another case of the method, mapping the text phrases in the corpus to a set of word embeddings comprises performing at least one of GloVe and fastText.

In yet another case of the method, the taxonomy comprises a graph with concepts at each vertex and relationships between respective concepts at the edges connecting respective vertices.

In yet another case of the method, vectorizing the taxonomy to the set of node embeddings comprises performing node2vec embedding comprising: starting on the edges from each vertex and stopping at a vertex after a fixed number of steps, wherein each vertex visited during the steps is recorded as part of the graph neighbourhood.

In yet another case of the method, the method further comprising generating the mapping function, comprising: concatenating the word embeddings into a single multi-dimensional vector; and determining a linear mapping comprising a matrix multiplication of the points in the node embedding space and the single multi-dimensional vector, wherein the linear mapping is the mapping function.

In yet another case of the method, the method further comprising generating the mapping function, comprising training a convolutional neural network using phrase-concept pairs previous labelled for at least a portion of the taxonomy, the convolutional neural network taking as input the set of word embeddings and the set of node embeddings, the convolutional neural network comprising applying convolutional filters to the input vectors to generate feature maps, feeding the feature maps into a pooling layer, and projecting the output of the pooling layer to obtain an output of a reduced dimension, wherein the trained convolutional neural network is the mapping function.

In yet another case of the method, the method further comprising generating the mapping function, comprising: training a bidirectional long short term memory network using phrase-concept pairs previous labelled for at least a portion of the taxonomy, the bidirectional long short term memory network taking as input the set of word embeddings and the set of node embeddings, the bidirectional long short term memory network comprising multiple hidden cells followed by a projection layer, wherein the trained convolutional neural network is the mapping function.

In another aspect, there is provided a system for mapping of text phrases in a corpus to a taxonomy, the system comprising one or more processors and memory, the memory storing the corpus and taxonomy, the one or more processors in communication with the memory and configured to execute: an input module to receive the corpus and the taxonomy; a corpus module to map the text phrases in the corpus to a set of word embeddings in a word embedding space, where each sequence of word embeddings corresponds to individual words in one of the text phrases; a taxonomy module to vectorize the taxonomy to a set of node embeddings in a node embedding vector space; and a mapping module to map the set of word embeddings to the set of node embeddings using a mapping function, the mapping function outputting points in the node embedding space associated with sequences in the word embeddings; and an output module to output the mapping function.

In a particular case of the system, the input module further pre-processing the corpus, the pre-processing comprising at least one of splitting phrases into words, splitting sentences, adding spaces around punctuation marks, changing characters to lowercase, reformatting to one sentence per line, and concatenating files.

In another case of the system, mapping the text phrases in the corpus to a set of word embeddings comprises performing at least one of GloVe and fastText.

In yet another aspect of the system, the taxonomy comprises a graph with concepts at each vertex and relationships between respective concepts at the edges connecting respective vertices.

In yet another aspect of the system, vectorizing the taxonomy to the set of node embeddings comprises performing node2vec embedding comprising: starting on the edges from each vertex and stopping at a vertex after a fixed number of steps, wherein each vertex visited during the steps is recorded as part of the graph neighbourhood.

In yet another aspect of the system, the mapping module further generates the mapping function, comprising: concatenating the word embeddings into a single multi-dimensional vector; and determining a linear mapping comprising a matrix multiplication of the points in the node embedding space and the single multi-dimensional vector, wherein the linear mapping is the mapping function.

In yet another aspect of the system, the mapping module further generates the mapping function, comprising: training a convolutional neural network using phrase-concept pairs previous labelled for at least a portion of the taxonomy, the convolutional neural network taking as input the set of word embeddings and the set of node embeddings, the convolutional neural network comprising applying convolutional filters to the input vectors to generate feature maps, feeding the feature maps into a pooling layer, and projecting the output of the pooling layer to obtain an output of a reduced dimension, wherein the trained convolutional neural network is the mapping function.

In yet another aspect of the system, the mapping module further generates the mapping function, comprising: training a bidirectional long short term memory network using phrase-concept pairs previous labelled for at least a portion of the taxonomy, the bidirectional long short term memory network taking as input the set of word embeddings and the set of node embeddings, the bidirectional long short term memory network comprising multiple hidden cells followed by a projection layer, wherein the trained convolutional neural network is the mapping function.

Other aspects and features according to the present application will become apparent to those ordinarily skilled in the art upon review of the following description of embodiments of the invention in conjunction with the accompanying figures.

BRIEF DESCRIPTION OF THE DRAWINGS

Reference will now be made to the accompanying drawings which show, by way of example only, embodiments of the invention, and how they may be carried into effect, and in which:

FIG. 6 is a table of intrinsic evaluation accuracy test results according to an example experiment;

FIG. 7 is a table of intrinsic mean graph distance test results according to the example experiment;

FIG. 8 is a table of extrinsic accuracy test results according to the example experiment;

FIG. 9 is a table of extrinsic mean graph distance test results according to the example experiment;

FIG. 10 is a table of extrinsic accuracy test results according to the example experiment;

FIG. 11 is a table of extrinsic mean graph distance test results according to the example experiment;

FIG. 12 is a table of zero-shot evaluation accuracy test results according to the example experiment; and FIG. 13 is a table of zero-shot evaluation mean graph distance test results according to the example experiment.

Like reference numerals indicated like or corresponding elements in the drawings.

DETAILED DESCRIPTION OF THE EMBODIMENTS

Figure 1:
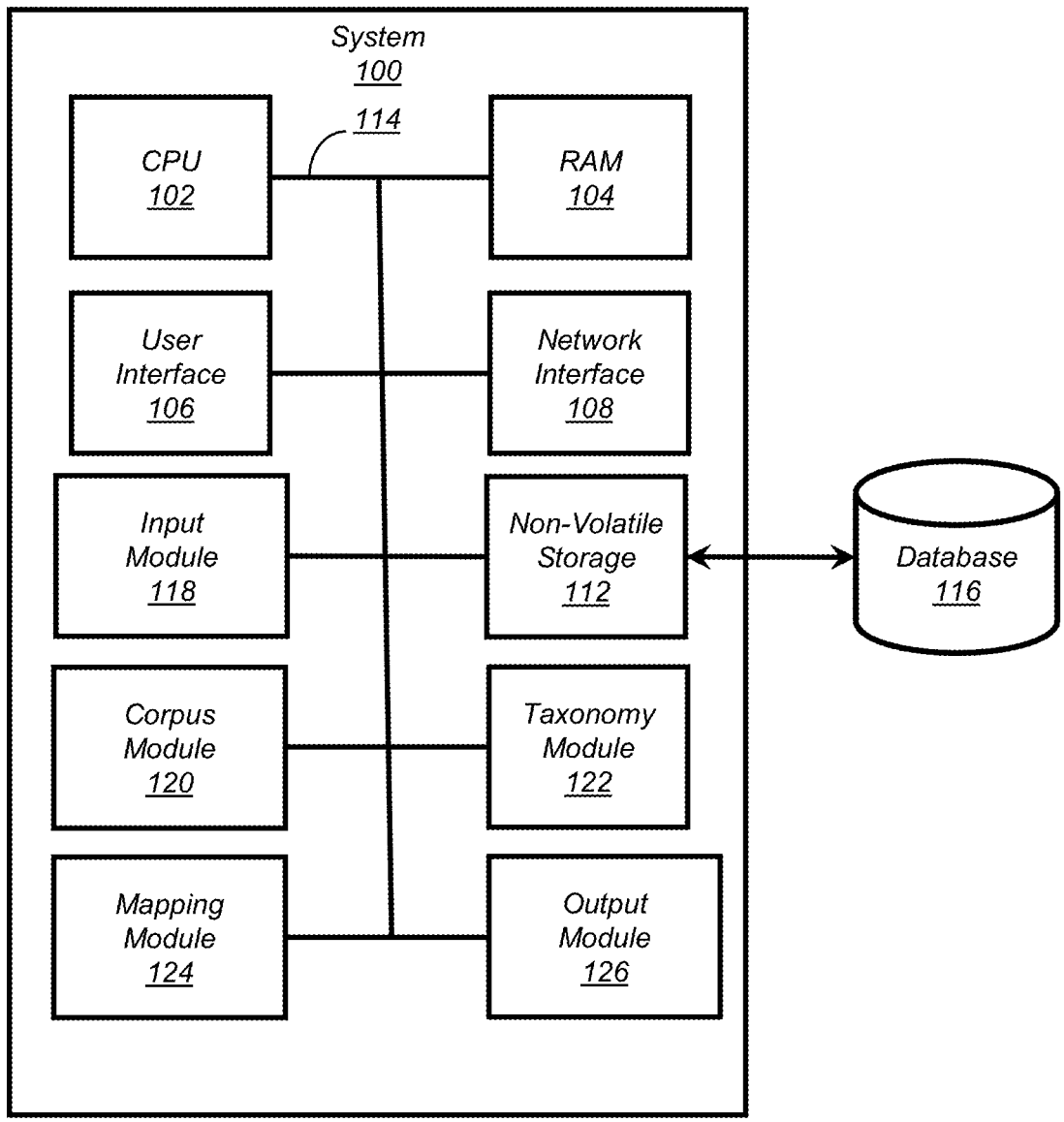
FIG. 1 is a schematic diagram of a system for mapping text values to a taxonomy according to an embodiment.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

The following relates generally to the mapping of general text phrases to a fixed taxonomy, and more specifically to computer-based method and system for mapping text phrases to a medical language taxonomy.

Figure 2:
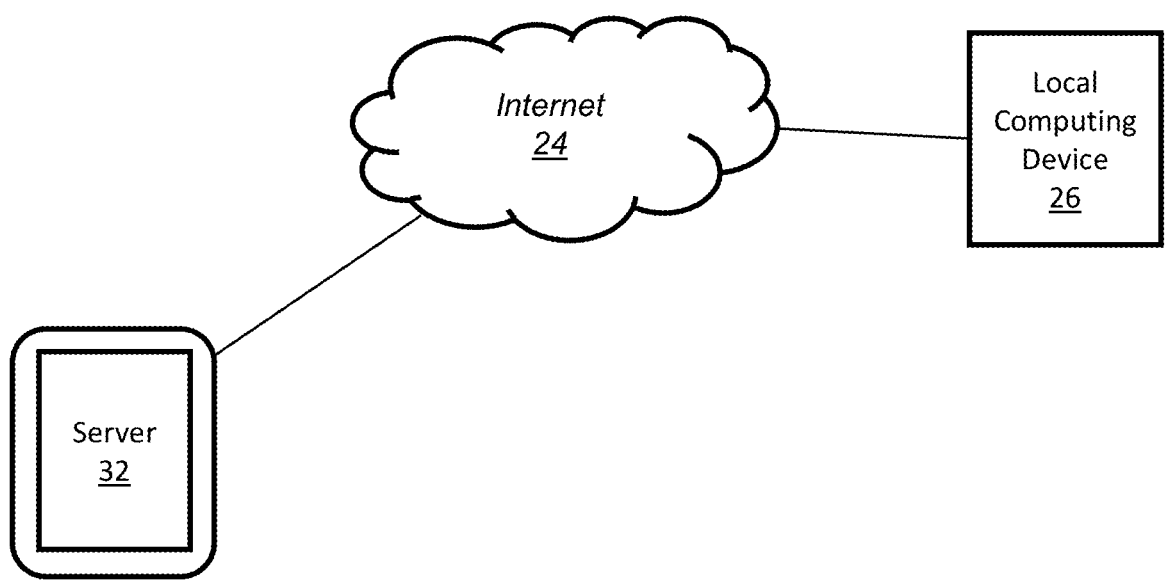
FIG. 2 is a schematic diagram showing the system of FIG. 1 and an exemplary operating environment.

Referring now to FIG. 1, a system 100 for mapping text to a taxonomy, in accordance with an embodiment, is shown. In this embodiment, the system 100 is run on a local computing device (26 in FIG. 2). In further embodiments, the local computing device 26 can have access to content located on a server (32 in FIG. 2) over a network, such as the internet (24 in FIG. 2). In further embodiments, the system 100 can be run on any suitable computing device; for example, the server (32 in FIG. 2).

In some embodiments, the components of the system 100 are stored by and executed on a single computer system. In other embodiments, the components of the system 100 are distributed among two or more computer systems that may be locally or remotely distributed.

FIG. 1 shows various physical and logical components of an embodiment of the system 100. As shown, the system 100 has a number of physical and logical components, including a central processing unit ("CPU") 102 (comprising one or more processors), random access memory ("RAM") 104, a user interface 106, a network interface 108, non-volatile storage 112, and a local bus 114 enabling CPU 102 to communicate with the other components. In some cases, at least some of the one or more processors can be graphical processing units. CPU 102 executes an operating system, and various modules, as described below in greater detail. RAM 104 provides relatively responsive volatile storage to CPU 102. The user interface 106 enables an administrator or user to provide input via an input device, for example a keyboard and mouse. The user interface 106 can also output information to output devices to the user, such as a display and/or speakers. The network interface 108 permits communication with other systems, such as other computing devices and servers remotely located from the system 100, such as for a typical cloud-based access model. Non-volatile storage 112 stores the operating system and programs, including computer-executable instructions for implementing the operating system and modules, as well as any data used by these services. Additional stored data can be stored in a database 116. During operation of the system 100, the operating system, the modules, and the related data may be retrieved from the non-volatile storage 112 and placed in RAM 104 to facilitate execution.

In an embodiment, the system 100 further includes a number of functional modules that can be executed on the CPU 102; for example, an input module 118, a corpus module 120, a taxonomy module 122, a mapping module 124, and an output module 126. In some cases, the functions and/or operations of the modules can be combined or executed on other modules.

An approach to mapping an arbitrary coding system to a taxonomy is to start with the phrases that describe each code. As the coding system should be understandable to human users, the phrases describing each code must provide enough information for them to be able to use it.

Historically, word embeddings have been widely used to capture the semantic meaning of words, phrases and even sentences. For example, word embeddings have been successfully applied in clinical settings to information retrieval, named entity recognition and patient outcome prediction tasks on unstructured text in EMR narratives. Specifically, this technique assigns real-valued vectors of a fixed length to individual words from a collection of documents, called a corpus. This vector representation is intended to capture the semantic relationships between words, so that synonyms lie close to each other, while unrelated words are far away. Accordingly, many algorithms have been developed and used to generate word embeddings; for example, GloVe and fastText.

A feature of word embedding algorithms is the use of contextual interchangeability as a proxy for relatedness in meaning. However, this feature can be a problem for some tasks, especially in the medical setting. For example, the terms "cold" and "viral respiratory infection" are highly related but are not often used interchangeably in the medical context. The use of contextual interchangeability as a proxy may lead the word algorithms to incorrectly position the vectors corresponding to these two terms very far from each other in the embedding space.

Additionally, in fields such as healthcare and biomedical research, the relationships between entities may contain valuable information, for example, by describing the interactions and causal relationships between diagnosis, medications and procedures, as well as genetic components. To document the complex relationships, large databases have been built, including biomedical knowledge graphs (e.g. PharmGKB, DrugBank), ontologies (e.g. Gene Ontology) and taxonomies such as International Statistical Classification of Diseases (ICD), and SNOMED CT.

Network topology may be used to analyze and represent the network structure of these biomedical databases. Such analysis may require high computational costs due to the high dimensionality and sparsity of these databases. Network embedding technologies may provide effective paradigms to solve the network analysis problem. Network embedding converts the network into a low-dimensional space while maximally preserving its structural properties. Network embedding algorithms have been developed to attempt to embed these graphs into vector spaces and then used to attempt to predict drug-drug interactions.

Contextual interchangeability may not provide a good metric of medical relatedness, as word embeddings cannot be directly used to map between coding systems. They may be used to capture semantic information from phrases that are used to describe such systems. In contrast, node embeddings generated from concepts in a medical taxonomy may be a better representation of medical relatedness, because they are intended to be built from relationships between medical concepts. In order to bridge the gap between these two embedding spaces, a mapping function is needed. This mapping function provided herein advantageously operates on the level of vector representations rather than original phrases and concepts. This can produce two important advantages: these vector spaces may be low-dimensional compared to hundreds of thousands of original concepts and the function learned from embeddings may be more generalizable and may then be easier to train.

Additionally, whenever there is scarcity of supervised data, machine learning models may fail to carry out reliable generalizations. Obtaining correctly labeled data may be costly and impractical for large datasets. One practical application of concept embedding is the zero-shot transformation of words and concepts that were missing in the training data (zero-shot learning). It can be possible to thus generalize the mapping function and accurately map unseen concepts, having only a few training examples per concept, because embedding training in both domains is an unsupervised task. In some cases, this can be done through nearest neighbour retrieval, where the closest embedding in the target space is selected according to a similarity metric.

Embodiments of the present disclosure provide a technological solution to the task of normalizing and linking phrases to a taxonomy, thereby advancing data interchangeability in healthcare and other fields. When applied, embodiments of the system can, for example, use electronic health records to generate an embedding that incorporates taxonomical medical knowledge to improve clinical predictive models.

Figure 3:
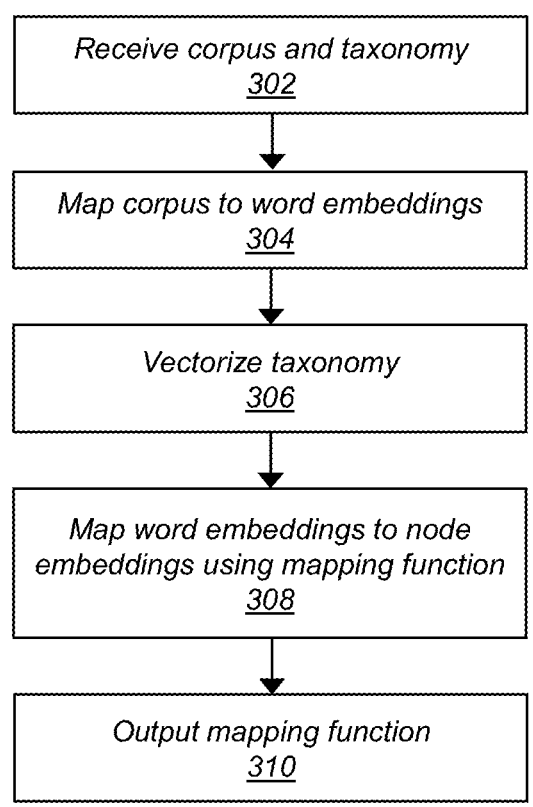
FIG. 3 is a flowchart of a method for mapping text values to a taxonomy according to an embodiment.
Figure 4:
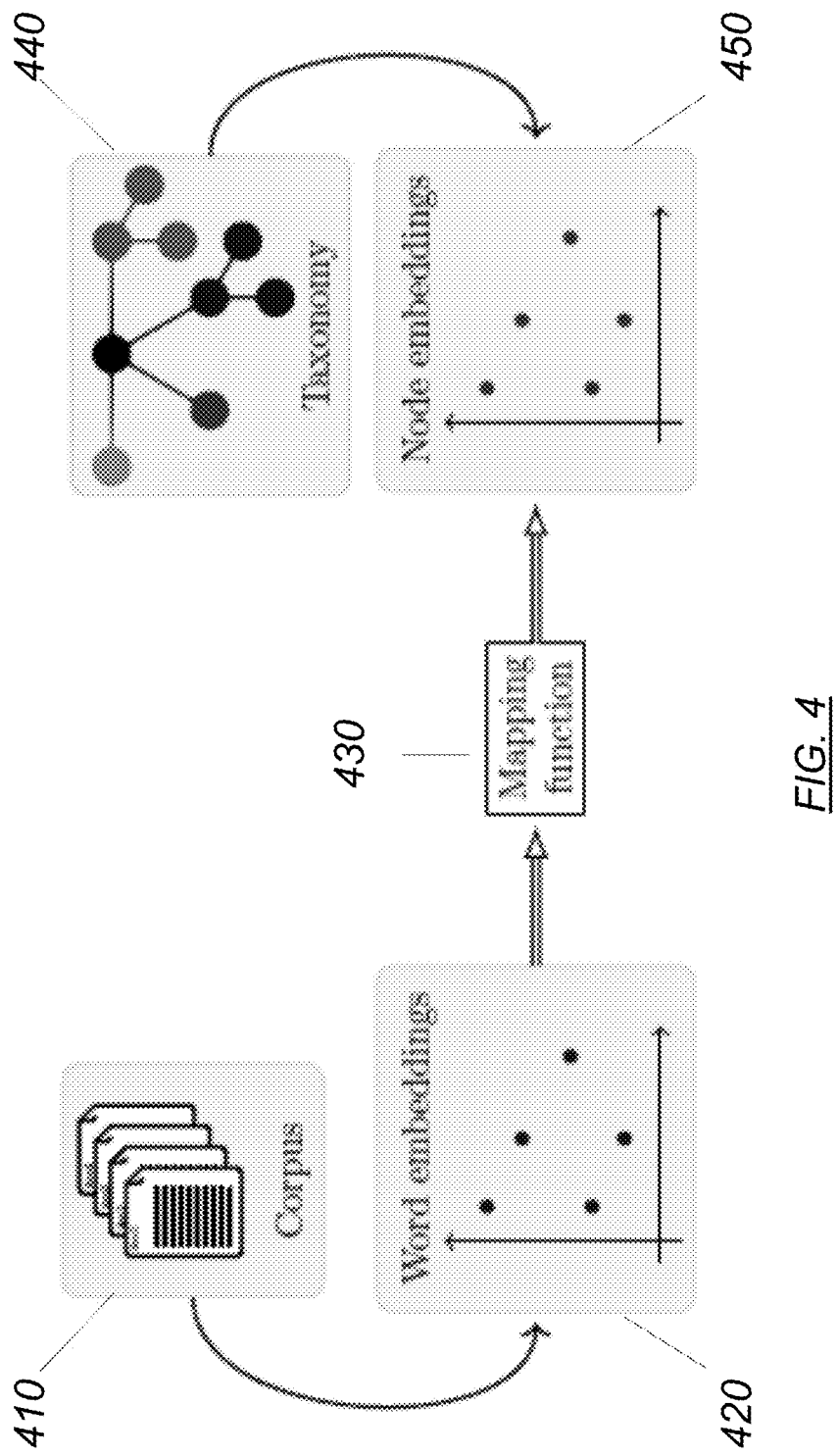
FIG. 4 is an example of a mapping function method according to an embodiment.

FIG. 3 illustrates a flowchart diagram of a method for mapping of text phrases in a corpus to a taxonomy 300, according to an embodiment. FIG. 4 illustrates a diagram of an example implementation of method 300. At block 302, the input module 118 receives the corpus 410 and the taxonomy 440; for example, from the database 116, the user interface 106, or the network interface 108. In some cases, the corpus 410 and the taxonomy 440 can be received together, and in other cases, can be received separately. In some cases, the corpus 410 can include, or can be, a lexicon. At block 304, the corpus module 120 maps the corpus 410 to word embeddings 420. At block 306, the taxonomy module 122 vectorizes the taxonomy 440 using node embeddings 450. At block 308, the mapping module 124 the set of word embeddings to the set of node embeddings using a mapping function 430. At block 310, the output module 126 outputs the mapping function 430; for example, to the database 116, the user interface 106, or the network interface 108.

Word embeddings 420, when, for example, trained on a biomedical corpus can generally capture the semantic meaning of medical concepts better than embeddings trained on an unspecialized set of documents. In a biomedical example, to construct the corpus, the corpus module 120 can use one or more of open access papers (for example, from PubMed), free text admission and discharge notes (for example, from MIMICIII Clinical Database), narratives (for example, from the US Food and Drug Administration (FDA) Adverse Event Reporting System (FAERS)), and other documents (for example, a part of the 2010 Relations Challenge from i2b2).

In some cases, the corpus module 120 can preprocess the documents used to construct the corpus 410. For example, the preprocessing may include splitting sentences, adding spaces around punctuation marks, changing characters to lowercase, and reformatting to one sentence per line. The preprocessing may also include concatenating files into a single document. In an example, using the above-mentioned sources, a single document can comprise 235 million sentences and 6.25 billion words to create the corpus 410. The corpus 410 may then be used for training word embedding algorithms for mapping the word embeddings 420.

For the biomedical example described herein, two algorithms may be used for learning word embeddings: examples of which include Global Vectors (GloVe) and fastText. A distinction between them is the treatment of words that are not part of the training vocabulary: GloVe creates a special out-of-vocabulary token and maps all of these words to this token's vector, while fastText uses subword information to generate an appropriate embedding.

GloVe is built on global matrix factorization and local context window. GloVe learns the ratios of co-occurrence probabilities to better discriminate subtleties in term-term relevance and boost performance on word analogy tasks. In GloVe, the embeddings can be optimized directly such that a dot product of two word vectors equals a log of a number of times two words will occur near each other.

fastText is a word embedding algorithm that, instead of learning vectors for words directly, represents each word as an n-gram of characters. For instance, the fastText representation of "biomedical" with n=3, is <bi, bio, iom, ome, med, edi, dic, ica, al>. This allows the embeddings to understand suffixes and prefixes and helps capture the meaning of shorter words. In some cases, once the word has been represented using character n-grams, a skip-gram model can be trained to learn the embeddings. This model is generally considered to be a bag of words model with a sliding window over a word because internal structure of the word is generally not taken into account. As long as the characters are within this window, the order of the n-grams generally does not matter. In this way, fastText generally performs well for rare words. Thus, even if a word was not seen during training, the new word can be broken down into n-grams to get its embeddings.

In an example, vector space dimensionality can be set to 200 and the minimal number of word occurrences to 10 for both word embedding algorithms; producing a vocabulary of 3.6 million tokens.

The taxonomy module 122 can use any suitable taxonomy 430 to which the mapping module 124 maps phrases. For the biomedical example described herein, a 2018 international version of SNOMED CT may be used as the target graph G=(V, E). In this example, the vertex set V consists of 392 thousand medical concepts and the edge set E is composed of 1.9 million relations between the vertices; including is_a relationships and attributes such as finding_site and due_to. In this example, snomed is used as a target taxonomy. In this way, the medical concepts present in the taxonomy can be treated as a node in the taxonomy graph, and the relationships between these medical concepts can be treated as an edge in the taxonomy graph; for example, is_a and finding_site To construct taxonomy embeddings, taxonomy module 122 can use any suitable embedding approach. In an example, the taxonomy module 122 can use the node2vec approach. In this example approach, a random walk may start on the edges from each vertex $v \in V$ and stop after a fixed number of steps (20 in the present example). All the vertices visited by the walk may be considered part of the graph neighbourhood N(v) of v. Following a skip-gram architecture, in this example, a feature vector assignment function $v \rightarrow f_{n2v}(v) \in \mathbb{R}^{128}$ may be selected by solving an optimization problem:

$$f_{n2v} = \underset{f}{\operatorname{argmax}} \sum_{u \in V} \log \mathbb{P}[N(u) \mid f(u)]$$

using, for example, stochastic gradient descent and negative sampling. Where f is a mapping function of vertex vector u, which is a multi-layer of neural networks.

Figure 5:
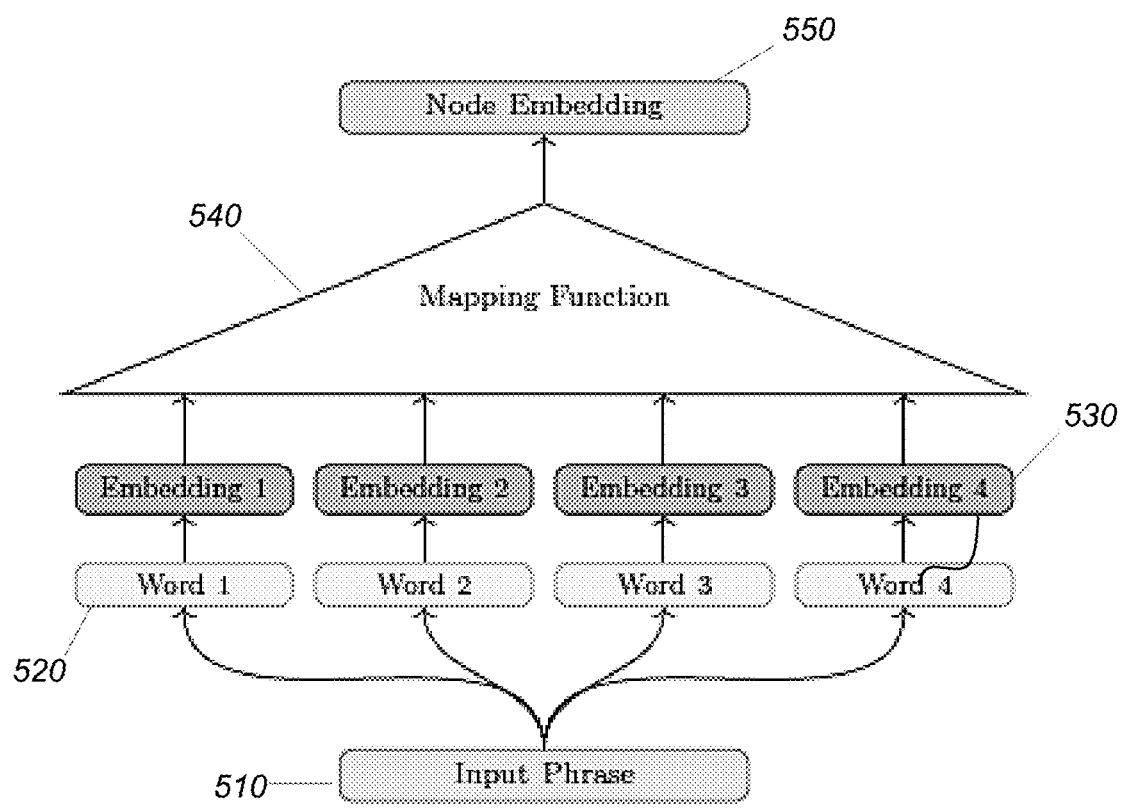
FIG. 5 is an example of a mapping function method according to an embodiment.

The mapping module 124 can map between phrases and concepts in the target taxonomy by associating points in the node embedding vector space to sequences of word embeddings corresponding to individual words in a phrase. As illustrated in FIG. 5, in some cases, an input phrase 510 from the corpus can be split into words 520 that are converted to word embeddings 530 and fed into the mapping function 540, with the output of the function being a point in the node embedding space 530 (in the above example, $\mathbb{R}^{128}$). Thus, given a phrase consisting of n words with the associated word embeddings $w_1, \ldots, w_n$, the mapping function is $m:(w_1, \ldots w_n) \to p$, where p is a point in the node embedding vector space (in the above example, $p \in \mathbb{R}^{128}$). In some cases, to complete the mapping, concepts in the taxonomy whose node embeddings are the closest to the point p are used. In this way, the mapping function can map the sequence of input vectors to target vectors (p), which in this example is in a 128 dimensional node embedding vector space. To find the corresponding node related to those words, the mapping module 124 determines the closest node to the target vectors (p). In an example experiment of the biomedical example, the present inventors tested two measures of closeness in the node embedding vector space $\mathbb{R}^{128}$: Euclidean $\ell_2$ distance and cosine similarity; that is $$\ell_2 \text{ distance}(p, q) = \|p - q\| = \sqrt{(p-q) \cdot (p-q)},$$
$$\cos \text{ similarity}(p, q) = \frac{p \cdot q}{\|p\|\|q\|},$$

In some cases, for example to compute the top-k accuracy of the mapping, a list of k closest concepts was used.

The exact form of the mapping function m may vary. Three different architectures are provided as examples herein, although others may be used: a linear mapping, a convolutional neural network (CNN), and a bidirectional long short term memory network (Bi-LSTM). In some cases, phrases can be padded or truncated. For example, in the above example, padded or truncated to be exactly 20 words long to represent each phrase by 20 word embeddings $w_1, \ldots w_{20} \in R^{200}$ in order to accommodate all three architectures.

Linear mapping can be used as a baseline. In this way, it can be examined whether the input (sequence of word embeddings) is linearly mappable to the output (node embeddings). CNN can be used to learn position and scale invariant structures in the data, especially if the data has a spatial relationship. Thus, a CNN can be used to capture an order relationship between words in the input text. In most cases, to train the CNN model, the input should have the same size, so it requires adding or truncating the sequence of input. Bi-LSTM is a type of recurrent neural networks (RNNs) model. RNNs are especially adept at learning sequence prediction problems; in this way, Bi-LSTM can be used to capture long term dependency in the sequence of word embeddings. While Bi-LSTM can work with inputs of variable length, in some cases, for the sake of faster training, in the training phase, the data in a training batch in made the same length. In such cases, in each batch, the length of the word vectors are set to be equal to the longest word vector in that batch.

For linear mapping, a linear relationship can be derived between the word embeddings and the node embeddings. In the above example, 20 word embeddings may be concatenated into a single 4000 dimensional vector w, and the linear mapping given by p=m(w)=Mw for a 4000×128 matrix M.

For the CNN, the mapping module 124 can use convolutional filters of different sizes to the input vectors. The feature maps produced by the filters can then be fed into a pooling layer followed by a projection layer to obtain an output of desired dimension. In an example, filters representing word windows of sizes 1, 2, 3, and 5 may be used, followed by a maximum pooling layer and a projection layer to 128 output dimensions. CNN is a nonlinear transformation that can be advantageously used to capture complex patterns in the input. Another advantageous property of the CNN is an ability to learn invariant features regardless of their position in the phrase. The input to the CNN is a sequence of word embeddings.

Bi-LSTM is also a non-linear transformation. For the Bi-LSTM, the mapping module 124 can use this type of neural network to operate by recursively applying a computation to every element of the input sequence conditioned on the previous computed results in both forward and backward direction. This structure allows the networks to have both backward and forward information about the sequence at each time step. In this way, the Bi-LSTM's backward propagation preserves information from the future, allowing preservation of information from both past and future. Bi-LSTM may be used for learning long distance dependencies in its input. In an example, the model can be initialized randomly and have a tan h activation function. In the above example, the mapping module 124 can use a Bi-LSTM to approximate the mapping function m by building a single Bi-LSTM cell with 200 hidden units followed by a projection layer to 128 output dimensions.

In an example experiment conducted by the present inventors, training data was gathered consisting of phrase-concept pairs from the taxonomy itself. Training data includes phrase-concept pairs from the taxonomy; where input is a phrase and a respective target is its corresponding concept in the taxonomy. As nodes in SNOMED CT may have multiple phrases describing them (synonyms), each synonym-concept pair was considered separately for a total of 269K training examples. To find the best mapping function m·in each of the three architectures described above, the supervised regression problem $$m_* = \underset{m}{\arg\min} \sum_{(phase, node)} \|m(\text{phrase}) - f_{n2v}(\text{node})\|_{\ell_2}^2$$

was solved using the Adam optimizer for 50 epochs.

In the example experiment, the three mapping function architectures were evaluated to assess performance using a random hold-out test set of 10 thousand phrase-concept pairs. The robustness and generalizability of the top performing architectures were tested on a new lexicon consisting of 8.9 thousand phrases from ICD-9-CM. Finally, the zero-shot learning capability of the mapping module 124 was tested by randomly selecting a thousand concepts from the training set, removing all associated 3.4 thousand phrase-concept pairs from the training dataset, and retraining the system. The zero-shot learning performance was evaluated by mapping the removed phrases to concepts that were never seen before.

The tests considered two performance metrics: accuracy and mean graph distance. In the present examples, accuracy is the proportion of test phrases that are mapped exactly to their corresponding concept (higher is better). This metric may be used for classification-based approaches. Mean graph distance is the average graph distance (length of the shortest path) in the taxonomy between the target concept and the predicted concept (lower is better). This metric tells how far the predicted concept is from the exact match, and low scores are evidence for predictions that are immediate neighbours of the target concept, that is its children or parents.

It may be possible that two distinct concepts were embedded to the exact same location in the node embedding space. Since the mapping procedure involved nearest neighbor searches, the performance metrics for the top-k results of these searches were computed for k=1; 5; 10; 20; 50.

For intrinsic evaluation, a random hold-out test set of 10K phrase-concept pairs was used to find the top performing architectures. The accuracy results are provided in FIG. 6, and the graph distance results are provided in FIG. 7. The overall top performing mapping module was the Bi-LSTM mapping function on top of fastText embeddings. Using cosine similarity may yield better accuracy scores, while the $\ell_2$ distance may provide for slightly smaller average graph distances.

To check the robustness and generalizability of the mapping system, an extrinsic evaluation task was created consisting of 8.9K ICD-9-CM phrases mapped by medical experts from U.S. National Library of Medicine (2015) to a unique SNOMED CT concept. The accuracy results are in provided in FIG. 8, and the graph distance results are provided in FIG. 9. The Bi-LSTM model on fastText was again the top performing mapping module experiment with all the predicted concepts close to the exact match in terms of taxonomy distance, as either synonyms, parents, or children of the exact match concept from 392 thousand nodes.

This test set was also applied to adjust for the effect of extra knowledge of source phrases on mapping to the target taxonomy. When the search space was reduced to 7.5 thousand concepts that have at least one ICD-9-CM phrase mapped to them, from the 392 thousand concepts originally used, the accuracy and mean graph distance results improved significantly as shown in FIGS. 10 and 11. Therefore, extra knowledge about the category of the taxonomy may allow a reduction in the search space and a corresponding boost to the performance of mapping module.

To evaluate the zero-shot learning capability, 1 thousand concepts from the taxonomy were randomly selected from those that appeared in the training set. All 3.4 thousand phrase-concept pairs associated to the selected concepts were removed from the training set, and used as the test set. The Bi-LSTM mapping network was retrained from a starting state using the new training set, such that all of the targets in the zero-shot test set were never seen before by the mapping function. The accuracy and mean graph distance results are provided in FIGS. 12 and 13 and show comparable results to the intrinsic task evaluations, and the mapping system may be general enough to be able to map to unseen concepts in the training set.

Thus, as demonstrated in the above examples, the system 100 can be used to approach and solve several categories of problems. One problem is that of named entity recognition (NER), the task of extracting relevant concepts from free text. Once extracted, such concepts need to be mapped to a taxonomy of known entities. The system 100 can advantageously solve this mapping problem. Given EMR data, the system 100 can be used to annotate medical concepts in documents in the data. A part of the text can be selected as a candidate, and then the system 100 determine its correspondent concept in the taxonomy.

Another problem is finding a representation for a phrase that can capture all the information in its sequence of words for natural language processing. The mapping module 124 can apply the mapping function as an encoding model that is generating a representation for medical phrases. This representation has been trained and supervised using the concepts information in the taxonomy, and also represents their taxonomy position and the structure of their neighbourhood in the taxonomy. Thus, this supervised representation of the medical phrases may be used in different tasks (for example, medical prediction) using transfer learning techniques.

A practical application of embedding mappings according to embodiments of the present system 100 is the zero-shot transformation of concepts that are missing in the training data (zero-shot learning). It can be possible to generalize the mapping function and accurately map unseen concepts, having only a few training examples per concept, because embedding training in both domains is an unsupervised task. In some cases, this can be performed with nearest neighbour retrieval, where the closest embedding in the target space is selected according to a similarity metric. In another application of concept embeddings, the system 100 may be used for data pre-processing when the training data is difficult to obtain. Given a concept description (sequence of words), the system 100 can map it to a node embedding as a better representation of the description, as a preprocessing for other tasks.

The presently disclosed embodiments can be embodied in other specific forms without departing from the spirit or essential characteristics thereof. Certain adaptations and modifications of the invention will be obvious to those skilled in the art. Therefore, the presently discussed embodiments are considered to be illustrative and not restrictive, the scope of the invention being indicated by the appended claims rather than the foregoing description and all changes which come within the meaning and range of equivalency of the claims are therefore intended to be embraced therein.

The invention claimed is:

1. A computer-implemented method for mapping of text phrases in a corpus of biomedical data to a biomedical taxonomy, the method comprising:

receiving the corpus of biomedical data and the biomedical taxonomy;

mapping the text phrases in the corpus to a set of word embeddings in a word embedding space, where each sequence of word embeddings corresponds to individual words in one of the text phrases;

vectorizing the taxonomy to a set of node embeddings in a node embedding vector space, the taxonomy comprises a graph with concepts at each vertex and relationships between respective concepts at the edges connecting respective vertices mapping the set of word embeddings in the word embedding space to the vectorized set of node embeddings in the node embedding vector space using a mapping function between the spaces, the mapping function outputting points in the node embedding space associated with sequences in the word embeddings, the mapping function determined using a trained machine learning model, the machine learning model taking as input the set of word embeddings and the set of node embeddings and trained using phrase-concept pairs previous labelled for at least a portion of the taxonomy; and annotating text phrases in the corpus of biomedical data with the biomedical taxonomy using the mapping function, and outputting the annotated text phrases to an interface.

2. The method of claim 1, further comprising pre-processing the corpus, the pre-processing comprising at least one of splitting phrases into words, splitting sentences, adding spaces around punctuation marks, changing characters to lowercase, reformatting to one sentence per line, and concatenating files.

3. The method of claim 1, wherein mapping the text phrases in the corpus to a set of word embeddings comprises performing at least one of GloVe and fastText.

4. The method of claim 1, wherein vectorizing the taxonomy to the vectorized set of node embeddings comprises performing node2vec embedding comprising: starting on the edges from each vertex and stopping at a vertex after a fixed number of steps, wherein each vertex visited during the steps is recorded as part of the graph neighbourhood.

5. The method of claim 1, wherein the machine learning model comprises a convolutional neural network, the convolutional neural network comprising applying convolutional filters to the input vectors to generate feature maps, feeding the feature maps into a pooling layer, and projecting the output of the pooling layer to obtain an output of a reduced dimension.

6. The method of claim 1, wherein the machine learning model comprises a bidirectional long short term memory network, the bidirectional long short term memory network comprising multiple hidden cells followed by a projection layer.

7. A system for mapping of text phrases in a corpus of biomedical data to a biomedical taxonomy, the system comprising one or more processors and memory, the memory storing the corpus and taxonomy, the one or more processors in communication with the memory and configured to execute:
   an input module to receive the corpus of biomedical data and the biomedical taxonomy;
   a corpus module to map the text phrases in the corpus to a set of word embeddings in a word embedding space, where each sequence of word embeddings corresponds to individual words in one of the text phrases;
   a taxonomy module to vectorize the taxonomy to a set of node embeddings in a node embedding vector space, the taxonomy comprises a graph with concepts at each vertex and relationships between respective concepts at the edges connecting respective vertices;
   a mapping module to map the set of word embeddings in the word embedding space to the vectorized set of node embeddings in the node embedding vector space using a mapping function between the spaces, the mapping function outputting points in the node embedding space associated with sequences in the word embeddings, the mapping function determined using a trained machine learning model, the machine learning model taking as input the set of word embeddings and the set of node embeddings and trained using phrase-concept pairs previous labelled for at least a portion of the taxonomy, and to annotate text phrases in the corpus of biomedical data with the biomedical taxonomy using the mapping function; and
   an output module to output the annotated text phrases to an interface.

8. The system of claim 7, the input module further pre-processing the corpus, the pre-processing comprising at least one of splitting phrases into words, splitting sentences, adding spaces around punctuation marks, changing characters to lowercase, reformatting to one sentence per line, and concatenating files.

9. The system of claim 7, wherein mapping the text phrases in the corpus to a set of word embeddings comprises performing at least one of GloVe and fastText.

10. The system of claim 7, wherein vectorizing the taxonomy to the vectorized set of node embeddings comprises performing node2vec embedding comprising: starting on the edges from each vertex and stopping at a vertex after a fixed number of steps, wherein each vertex visited during the steps is recorded as part of the graph neighbourhood.

11. The system of claim 7, wherein the machine learning model comprises a convolutional neural network, the convolutional neural network comprising applying convolutional filters to the input vectors to generate feature maps, feeding the feature maps into a pooling layer, and projecting the output of the pooling layer to obtain an output of a reduced dimension.

12. The system of claim 7, wherein the machine learning model comprises a bidirectional long short term memory network, the bidirectional long short term memory network comprising multiple hidden cells followed by a projection layer.

* * * * *